United States Patent [19]

Dines

[11] Patent Number: 5,074,863
[45] Date of Patent: Dec. 24, 1991

[54] DISPOSABLE RETRACTABLE SURGICAL INSTRUMENT

[76] Inventor: Lenna V. Dines, 8760 Kendall, Richmond, Mich. 48062

[21] Appl. No.: 596,214

[22] Filed: Oct. 12, 1990

[51] Int. Cl.⁵ ............................................. A61B 17/32
[52] U.S. Cl. .................................. 606/41; 242/107.6; 606/45
[58] Field of Search ................ 242/107.6; 606/34, 41, 606/45

[56] References Cited

U.S. PATENT DOCUMENTS

| | | | |
|---|---|---|---|
| 3,880,380 | 4/1975 | Sugiura | 242/107.6 |
| 3,959,608 | 5/1976 | Finlayson et al. | 191/12.2 R |
| 4,068,383 | 1/1978 | Krebs | 242/107.6 |
| 4,109,223 | 8/1978 | Tenkman | 606/34 |
| 4,174,816 | 11/1979 | Olson | 242/47.5 |
| 4,259,066 | 3/1981 | Pietschmann | 433/78 |
| 4,270,708 | 6/1981 | Vonk | 242/107.6 |
| 4,499,341 | 2/1985 | Boyd | 191/12.4 |
| 4,557,436 | 12/1985 | Drake | 242/47.5 |
| 4,726,536 | 2/1988 | Lerner et al. | 242/100.1 |
| 4,726,538 | 2/1988 | Kovacik et al. | 242/107 |
| 4,735,377 | 4/1988 | Zuehsow | 242/107 |
| 4,834,208 | 5/1989 | Kagami et al. | 180/268 |
| 4,901,938 | 2/1990 | Cantley | 242/107.6 |

*Primary Examiner*—Ruth S. Smith
*Assistant Examiner*—Robert L. Nasser, Jr.
*Attorney, Agent, or Firm*—Brooks & Kushman

[57] ABSTRACT

A sterile surgical cord reel mechanism, for use in electrical surgical instruments, which retracts the power cord while the instrument is not in use. The assembly comprises a lightweight housing, which can be clipped to a surgical blanket, and within the housing a freely rotating spool onto which the electrical power cord will retract. The fixed end of the power cord has an electrical connector attached to it, while the extensible end is attached to a surgical instrument. As the surgical instrument is pulled from the spool, the spool rotates against the bias of the spring. A retraction brake system switch affixed to the housing holds the power cord in place until released, whereupon the power cord rewinds onto the spool.

6 Claims, 2 Drawing Sheets

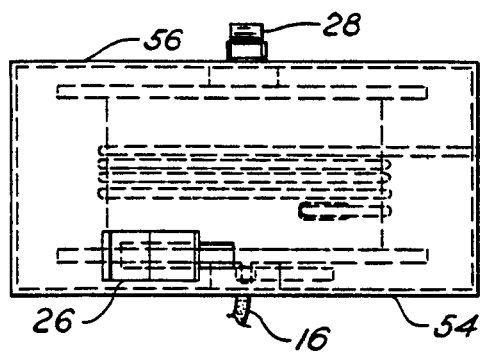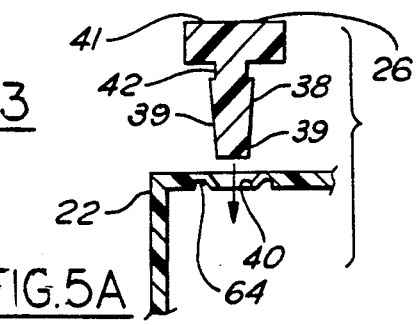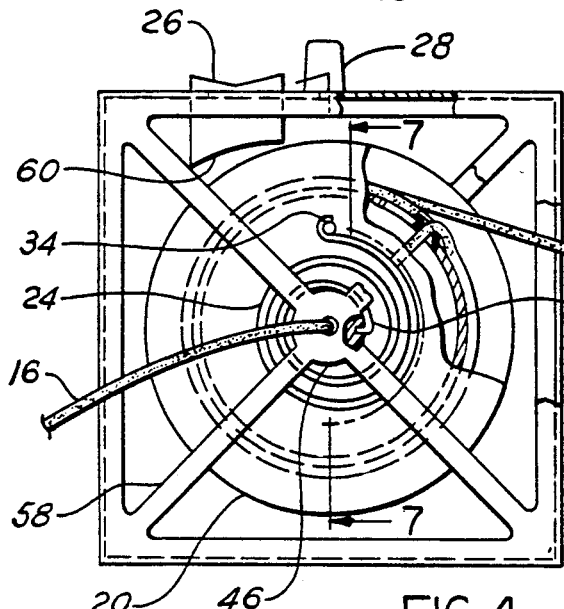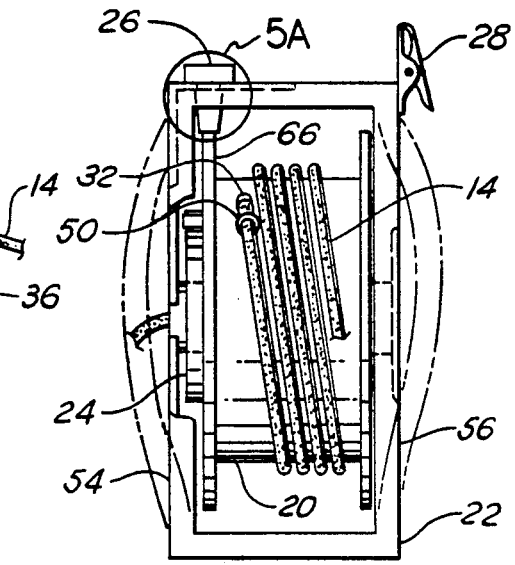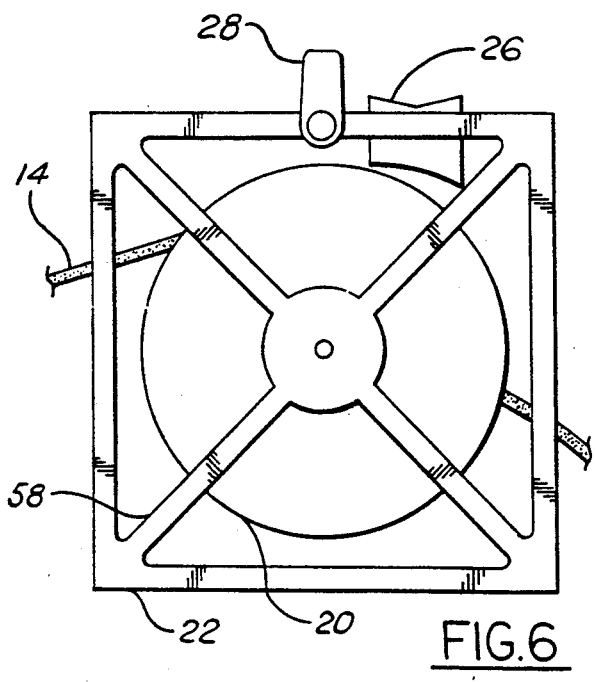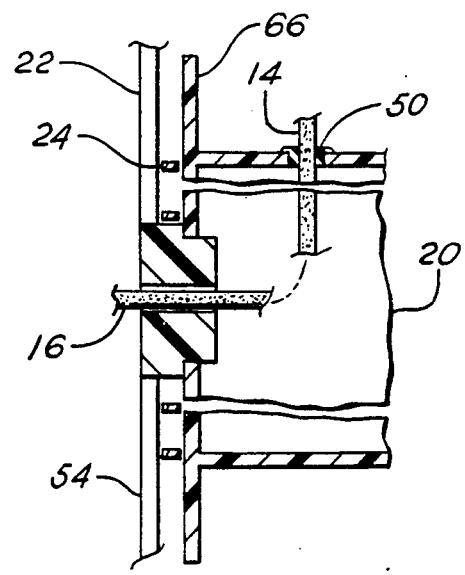

DISPOSABLE RETRACTABLE SURGICAL INSTRUMENT

TECHNICAL FIELD

The present invention is related to surgical instruments and particularly to a disposable retractable electrical surgical knife.

BACKGROUND ART

While one may not find a definition in the common day-to-day laymen's dictionary, a bovie knife, as it has come to be called, is an electrical knife used by a surgeon in cutting or cauterizing muscle fibers and the like of persons. Normally, it is not used on the skin. It is energized by, or utilizes, a direct current power source which is normally adjusted by the surgeon to an appropriate output voltage for accomplishing the particular task at hand. The bovie knife is one of many surgical instruments which will lie at the side of the surgeon during any operation and which must be readily available to the surgeon throughout the period of the operation. The problem that currently exists is that the bovie knife, by its nature, depends from the end of a long power cord extending from the power source. This power cord has a tendency to become tangled at the operating table, and by its very nature, the long cord tends to get in the way of the surgeon as he or she may be performing other operations.

There thus arises a need for an electrical surgical knife that can be conveniently stowed in place convenient to the surgery being performed and conveniently brought or manipulated by the surgeon while in use during the surgery being performed.

SUMMARY OF INVENTION

The present invention contemplates an electrical surgical instrument which may be conveniently stowed at the reach of the surgeon within the area of the surgery.

The present invention also contemplates an electrical surgical instrument which may be conveniently manipulated by the surgeon from a place close at hand to the specific areas of surgery and then returned to its original resting place.

The present invention further contemplates an electrical surgical instrument having a retractor mechanism for conveniently manipulating the surgical instrument into and out of the area of the surgery being performed.

The invention also contemplates an electrical surgical instrument accomplishing the aforesaid objectives which is inexpensive, easy to sterilize, disposable, and so simplistic an operation that the possibilities of any malfunction are nil.

The above objects and other objects, features and advantages of the present invention are readily apparent from the following detailed description of the best mode for carrying out the invention when taken in connection with the accompanying drawings.

BRIEF DESCRIPTION OF THE DRAWINGS

FIG. 3 is a top view of the retractor unit of the present invention showing the electrical power cord partially extended from the spool;

FIG. 4 is a side view of the retractor unit of the present invention shown with the back wall partially in section to illustrate the electrical power cord wound on the spool;

FIG. 5 is an end view of the retractor unit of the present invention showing the retraction switch and fastening clip;

FIG. 5A is an exploded view on an enlarged scale of the encircled portion 5A of FIG. 5 showing the retraction switch;

FIG. 6 is a view similar to FIG. 4, shown from the opposite side;

FIG. 7 is a fragmentary section on an enlarged scale taken along lines 7—7 of FIG. 4, illustrating the snap-in feature joining the spool to the housing.

BEST MODE FOR CARRYING OUT THE INVENTION

Figure 7A:
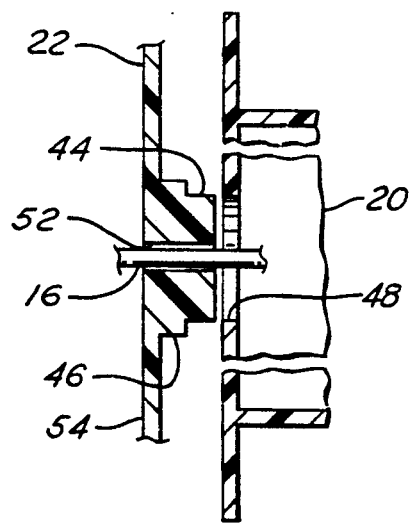
FIG. 7A is an exploded view of FIG. 7.

In FIGS. 1 through 7A, there is shown a retractor 10 and a bovie knife 12 attached by a retractable power cord designated generally by the numeral 13. The retractable end 14 of the power cord winds around the spool 20, and then is inserted into a slot 32 in the spool 20 and held in place by a grommet 50 as seen in FIGS. 5 and 7a. Slot 32 tapers circumferentially such that the narrowest portion of the slot is in the direction that the power cord is wound upon the spool. Thus, the power cord and grommet 50 are wedged fixedly in place at the slot. The fixed end 16 of the power cord then passes through a bore 52 in the center of the housing 22. There is a sufficient clearance between the fixed end 16 of the cord and the bore 52 in order to let the cord twist when the bovie 12 is extended or retracted. The fixed end 16 of the cord has a connector plug 18 at its end to allow hooking into a power source, not shown.

In actual size, the retractor spool will be approximately 3-5 inches in diameter. Thus, within a matter of several turns, the power cord end 14 can be extended 36 inches which is more than sufficient to have the surgical knife 12 move into and out of the area of operation.

The housing 22 encloses the spool 20 and allows it to rotate relative to the housing about a pair of journals 44 within side walls 54 and 56 as explained below. Looking at FIGS. 7 and 7A, the manner in which the spool 20 is held into the housing 22 is shown. The journals of both side walls 54 and 56 are constructed symmetrically, thus only one side wall journal arrangement need by discussed. The housing 22 has an annular notch forming an annular journal 44 on a circular centrally located hub 46 which slips into a bore 48 concentric about the central axis of the spool. The spool 20 is assembled into the housing 22 by bending out the sides 54 and 56 of the housing 22 as shown in phantom line in FIG. 5, which are made of a flexible plastic such as to increase the flexibility and maintain material costs at a minimum. The side walls are seen to comprise relatively narrow cross bars 58 extending from the corners of the housing and meeting in the center to form journals 44. There is sufficient clearance between journal 44 and the boundary surfaces of bore 48 such that the spool turns relatively freely on the journal 44 at the other side wall 56.

As shown in FIG. 4, the coil spring 24 is joined to the spool 20 and the housing 22 by a pin 34 attached to the spool and glue 36 attaching the spring 24 to the housing 22. The central axis of the coil spring 24 coincides with the central axis of the bore 48 in the housing 22. As the cord end 14 is pulled off of the spool 20, the spool rotates causing the spring 24 to wind up. Then, when the power cord end 14 is released, the spring 24 will unwind, rotating the spool, thus returning the power cord 14 to its original position.

Looking at FIGS. 4 and 5, there is shown a retraction brake switch 26, attached to the housing 22, and having a cam surface 60 which will cam up on the annular end wall or flange 66 of the spool 20 as the switch is manually slid toward the center of the housing to prevent the cord from retracting back onto the spool while in use. FIG. 5A shows a view of the retraction brake switch 26 attached to the housing 22 with an interference fit. The retractor brake switch 26 includes a head 41 at one end thereof and a flange portion 38 depending therefrom having a pair of side walls 39. The side walls 39 converge toward one another in the direction of the other end of the flange portion 38 opposite the head 41. Each side wall 39 includes a notch 42 extending the full width of the side walls 39 and immediately adjacent the head 41 to define an undercut portion of a predetermined width. The housing 22 includes a slot 40 disposed transversely of the axis of the spool and of a width substantially equal to the predetermined width. The flange portion 38 on the switch is inserted into a slot 40 on the housing 22 until the edges of the slot 40 catch in the notches 42 of the retraction brake switch 26. The edges of the slot 40 in the housing 20 have grooves 64 to allow the edges of the slot 40 to flex during assembly.

Figure 1:
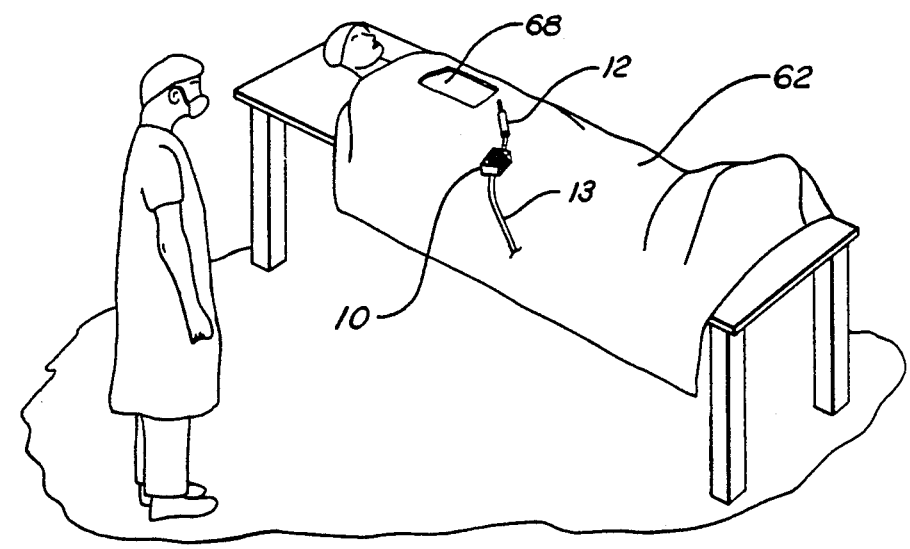
FIG. 1 is an overall view of the present invention as it would be used in a surgical operation.
Figure 2:
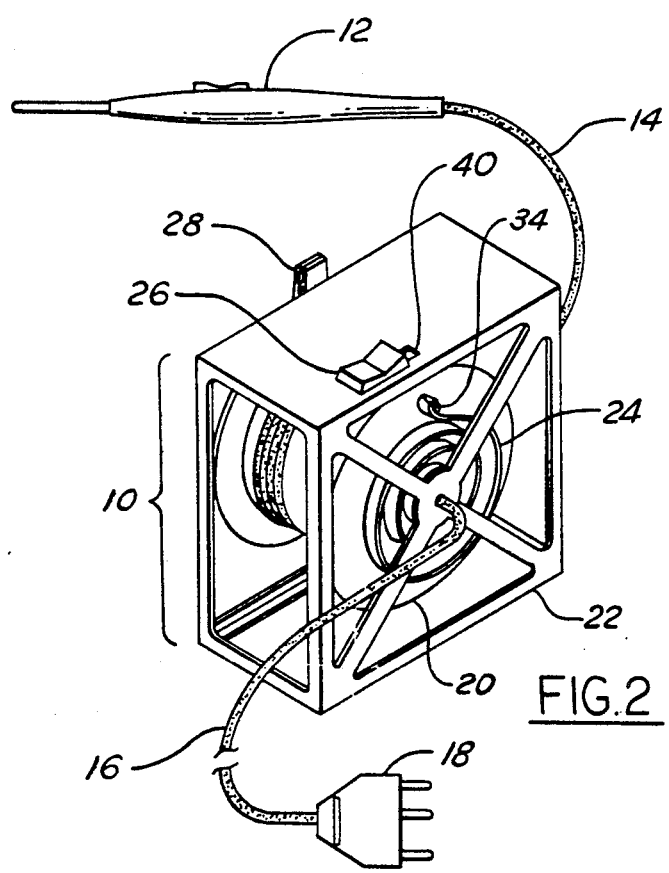
FIG. 2 is a perspective view of the disposable retractable surgical instrument showing its overall configuration in accordance with the present invention.

Referring to FIGS. 1 and 5, the housing is seen to include a fastening clip 28. The clip 28 is known as an alligator clip and includes a pair of spring-loaded, normally closed jaws, with one of the jaws being attached to the housing 22 by any suitable means. The clip 28 provides the means for attaching retraction unit 10 to the surgical blanket 62 thereby holding the retractor 10 in place.

The housing 22, spool 20, and spring 24 will be made of inexpensive materials. The housing 22 can be made of any flexible plastic material such as nylon. The spool 20 may also be made of this inexpensive plastic although the material of the spool need not necessarily be flexible. The spring 24 can be made of a resilient metal such as steel.

As a surgeon prepares to operate, the retractor unit 10 can be attached to a surgical blanket 62 on the operating table. Then, as the surgeon begins to use the bovie knife 12, he or she may pull the retractable cord 14, which is loosely coiled about the spool 20 out of the housing 22 thereby pulling out the knife far enough to reach the area of the operation 68 and rotating the spool 20 against the bias of the spring 24. The retractable cord end 14 can then be maintained in that position by engaging the retraction brake switch 26. Between uses, the retraction brake switch can be released resulting in the coil spring 24 uncoiling, thereby rotating the spool 20, and winding the retractable cord end 14 back onto it. After the operation is complete, the entire unit can then be disposed of.

While the best mode for carrying out the invention has been described in detail, those familiar with the art to which this invention relates will recognize alternative designs and embodiments for practicing the invention. Thus, the above described preferred embodiment is intended to be illustrative of the invention which may be modified within the scope of the following appended claims.

What is claimed is:

1. A disposable retractable electrical surgical instrument assembly comprising in combination:
   an electrically powered surgical instrument;
   an electrical power cord connected at one end to said surgical instrument and having at its opposite end means for connecting said power cord to an electrical energy source;
   a power cord retractor unit disposed between said ends of said power cord upon which said power cord is retractably wound;
   said retractor unit including a housing having spaced flexible side walls, said side walls including a journal means defining and axis, an annular spool mounted concentrically upon said journal means for rotation about said axis, and a spring means disposed between said spool and said housing for rotatively biasing said spool relative to said housing;
   said power cord being wound upon said spool and allowed to be pulled off the spool as the spool rotates about said axis in one direction, said spring means being loaded as said power cord is pulled off said spool whereby upon release of said extended power cord said spring means will return said power cord to its original position as said spool rotates in the direction opposite said one direction;
   said housing including a retractor brake switch means for halting the retraction of said power cord upon the spool at any point upon the extended length of said power cord;
   said retractor brake switch including a head at one end thereof and a flange portion depending therefrom having a pair of side walls, said side walls converging toward one another in the direction of the other end of said flange portion opposite said head, each side wall including a notch extending the full length of said side wall and immediately adjacent said head to define an undercut portion of a predetermined width, said housing including a slot disposed transversely of the axis of said spool and of a width substantially equal to said predetermined width, whereby said brake switch may be assembled to said housing and retained thereby by inserting said flange portion into said slot until the edges of said slot shall snap into place within said undercut portion.

2. The surgical instrument assembly of claim 1 wherein said retractor unit includes fastening means for affixing the retractor unit to a surgical blanket or the like whereby the retractor unit will remain fixed as the operator adjusts the length of said power cord.

3. The surgical instrument assembly of claim 2 wherein said fastening means includes an alligator clip having spring loaded jaws, one of said jaws being attached to said housing whereby said jaws may be attached to a surgical blanket to hold said housing in place.

4. The surgical instrument assembly of claim 3 wherein said spring means including a coil spring mounted concentrically upon said journal means and being affixed at one end thereof, the other end of said coil spring being affixed to said spool.

5. A disposable retractable electrical surgical instrument assembly comprising in combination:
   an electrically powered surgical instrument;

an electrical power cord connected at one end to said surgical instrument and having at its opposite end means for connecting said power cord to an electrical energy source;

a power cord retractor unit disposed between said ends of said power cord upon which said power cord is retractably wound;

said retractor unit including a housing having spaced flexible side walls, said side walls including a journal means defining an axis, an annular spool mounted concentrically upon said journal means for rotation about said axis, and a spring means disposed between said spool and said housing for rotatively biasing said spool relative to said housing;

said power cord being wound upon said spool and allowed to be pulled off the spool as the spool rotates about said axis in one direction, said spring means being loaded as said power cord is pulled off said spool whereby upon release of said extended power cord said spring means will return said power cord to its original position as said spool rotates in the direction opposite said one direction;

said side walls comprising narrow flexible cross bars which may be flexed outwardly to allow insertion of said spool into said housing;

said spool including a side wall having a bore;

said journal means on said housing including a hub member having an annular journal surface of a predetermined diameter; and said bore within said side wall of said spool being of a diameter slightly greater than that of said annular journal surface and being rotatably seated thereupon.

6. A disposable retractable electrical surgical instrument assembly comprising in combination:

an electrically powered surgical instrument;

an electrical power cord connected at one end to said surgical instrument and having at its opposite end means for connecting said power cord to an electrical energy source;

a power cord retractor unit disposed between said ends of said power cord upon which said power cord is retractably wound;

said retractor unit including a housing having spaced flexible side walls, said side walls including a journal means defining an axis, an annular spool mounted concentrically upon said journal means for rotation about said axis, and a spring means disposed between said spool and said housing for rotatively biasing said spool relative to said housing;

said power cord being wound upon said spool and allowed to be pulled off the spool as the spool rotates about said axis in one direction, said spring means being loaded as said power cord is pulled off said spool whereby upon release of said extended power cord said spring means will return said power cord to its original position as said spool rotates in the direction opposite said one direction;

said housing including a retractor brake switch means for halting the retraction of said power cord upon the spool at any point upon the extended length of said power cord;

said retractor brake switch means being slideable upon said housing transversely of said axis and including at its lowermost portion a cam surface portion;

said spool including a radially extended annular flange;

said cam surface portion being operable to engage and disengage from said annular flange as said brake switch means is slid upon said housing from one position to a second position to thereby arrest and release, respectively, the power cord at any point along its extended length on the spool;

said retractor brake switch means including a head at one end thereof and a flange portion depending therefrom having a pair of side walls, said side walls converging toward one another in the direction of the other end of said flange portion opposite said head, each side wall including a notch extending the full length of said side wall and immediately adjacent said head to define an undercut portion of a predetermined width, said housing including a slot disposed transversely of the axis of said spool and of a width substantially equal to said predetermined width, whereby said brake switch may be assembled to said housing and retained thereby by inserting said flange portion into said slot until the edges of said slot shall snap into place within said undercut portion;

said retractor unit including fastening means for affixing the retractor unit to a surgical blanket or the like whereby the retractor unit will remain fixed as the operator adjusts the length of said power cord;

said side walls comprised of narrow flexible cross bars which may be flexed outwardly to allow insertion of said spool into said housing;

said spool including a side wall having a bore concentric with said axis;

said journal means on said housing including a hub member having an annular journal surface of a predetermined diameter; and said bore within said side wall of said spool being of a diameter slightly greater than that of said annular journal surface and being rotatably seated thereupon.

* * * * *